(12) United States Patent
Lee et al.

(10) Patent No.: US 8,785,230 B2
(45) Date of Patent: Jul. 22, 2014

(54) LOCALIZED SURFACE PLASMON RESONANCE SENSOR USING CHALCOGENIDE MATERIALS AND METHOD FOR MANUFACTURING THE SAME

(71) Applicant: Korea Institute of Science and Technology, Seoul (KR)

(72) Inventors: Taek Sung Lee, Seoul (KR); Kyeong Seok Lee, Seoul (KR); In Ho Kim, Seoul (KR); Wook Seong Lee, Seoul (KR); Doo Seok Jeong, Gangwon-do (KR); Won Mok Kim, Seoul (KR); Byung Ki Cheong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/723,555

(22) Filed: Dec. 21, 2012

(65) Prior Publication Data

US 2013/0168789 A1     Jul. 4, 2013

(30) Foreign Application Priority Data

Dec. 28, 2011   (KR) .................. 10-2011-0144676

(51) Int. Cl.
*H01L 21/00*   (2006.01)
*H01L 31/18*   (2006.01)
*H01L 31/032*  (2006.01)

(52) U.S. Cl.
CPC .......... *H01L 31/186* (2013.01); *H01L 31/0324* (2013.01)
USPC ................. 438/49; 438/95; 257/431; 257/42; 257/E31.008

(58) Field of Classification Search
CPC .......................... H01L 31/186; H01L 31/0324
USPC ................. 438/49, 95; 257/431, 42, E31.008
IPC ....................................... H01L 31/186, 31/0324
See application file for complete search history.

(56) References Cited

U.S. PATENT DOCUMENTS

2004/0053354 A1*   3/2004   Ikawa et al. .................. 435/40.5
2009/0153869 A1    6/2009   Yamashita

FOREIGN PATENT DOCUMENTS

| JP | 2009-070768 A | 4/2009 |
| KR | 1020080050466 A | 6/2008 |
| KR | 1020080065801 A | 7/2008 |
| KR | 1020080111886 A | 12/2008 |
| KR | 1020100006842 A | 1/2010 |
| KR | 1020110042848 A | 4/2011 |
| WO | 2011/002117 A1 | 1/2011 |

OTHER PUBLICATIONS

J. Le Person, et al; "Surface Plasmon resonance in chalcogenide optical system", Sensors and Actuators B: Chemical; Mar. 2008, vol. 130, Issue 2, pp. 771-776.

(Continued)

*Primary Examiner* — Tu-Tu Ho
(74) *Attorney, Agent, or Firm* — Ladas & Parry LLP

(57) ABSTRACT

A localized surface plasmon resonance sensor may include a localized surface plasmon excitation layer including a chalcogenide material. The chalcogenide material may include: a first material including at least one of selenium (Se) and tellurium (Te); and a second material including at least one of germanium (Ge) and antimony (Sb). The localized surface plasmon excitation layer may be prepared by forming a thin film including the chalcogenide material and crystallizing the thin film to have a predetermined pattern by irradiating laser on the thin film.

8 Claims, 2 Drawing Sheets

(56) References Cited

OTHER PUBLICATIONS

S. Charnovych, et al; "Enhancement of photoinduced transformations in amorphous chalcogenide film via surface Plasmon resonances", Thin Solid Films, vol. 519, Issue 13, pp. 4309-4312; Available online Feb. 18, 2011.

Rajan Jha, et al; "Highly accurate surface Plasmon resonance based chalcogenide glass sensor for infrared Detection", ICOP 2009—International Conference on Optics and Photonics, CSIO, Chandigarh, India, Oct. 30-Nov. 1, 2009, pp. 1-4.

A.A. Popescu, et al; "Application of Vitreous As-S-Se Chalcogenides as Active Layer in Surface Plasmon Resonance Configuration", Digest Journal of Nanomaterials and Biostructures, vol. 6, No. 3, Jul.-Sep. 2011, pp. 1245-1252.

Changmeng Deng, et al; "Selective wet etching of $G3_2Sb_2Te_5$ phase-change thin films in thermal lithography with tetramethylammonium", Applied Physics A, Materials Science & Processing; Published online Apr. 9, 2011; 7 pages.

Joseph M. Luther, et al; "Localized surface Plasmon resonances arising from free carriers in doped quantum dots", Nature Materials, vol. 10, May 2011, pp. 361-366.

A. Mendoza-Galván et al; "Drude-like behavior of Ge:Sb:Te alloys in the infrared", Journal of Applied Physics, vol. 87, No. 2, Jan. 15, 2000, pp. 760-765.

* cited by examiner

LOCALIZED SURFACE PLASMON RESONANCE SENSOR USING CHALCOGENIDE MATERIALS AND METHOD FOR MANUFACTURING THE SAME

CROSS-REFERENCE TO RELATED APPLICATION

This application claims priority to Korean Patent Application No. 10-2011-0144676, filed on Dec. 28, 2011, and all the benefits accruing therefrom under 35 U.S.C. §119, the contents of which in its entirety are herein incorporated by reference.

BACKGROUND

1. Field

Embodiments relate to s localized surface plasmon resonance sensor using a chalcogenide material and a method for manufacturing same.

2. Description of the Related Art

Localized surface plasmon resonance is a phenomenon occurring when a collective oscillation of free electrons in a material is restricted inside a structure whose dimension is smaller than the wavelength of incident light. Since the resonance wavelength at which localized surface plasmons resonance is induced is very sensitively dependent on particle size and shape, change in surrounding medium, or the like, a biochemical sensor that can be utilized in the field of medicine, environment, etc. may be embodied using localized surface plasmon resonance. For example, Korean Patent Publication No. 10-2011-0042848 discloses an optical biosensor based on localized surface plasmon resonance.

As described in Korean Patent Publication No. 10-2011-0042848, precious metals such as gold (Au), silver (Ag) and copper (Cu) are frequently used to induce localized surface plasmon resonance. However, since the resonance wavelength of the localized surface plasmon resonance is usually in the visible region when such precious metals are used, only the change in the surrounding medium sensitive to light in the visible region can be detected.

The air coming out of the human lungs contain various biomarkers allowing diagnosis of diseases of individuals. But, since the wavelength allowing detection of the biomarkers is usually in the mid-infrared region, there is difficulty in detecting the biomarkers with the existing localized surface plasmon resonance sensors using precious metals.

To overcome this problem, efforts are made to broaden the resonance wavelength range by modifying the structure of the precious metal materials. However, the modification of the structure of the precious metal materials is not easy and it is much more favorable to choose other materials that operate well in the infrared region in terms of cost. Such materials may be semiconductor materials that exhibit properties comparable to those of metals in the infrared region although the density of electrons or carriers is smaller than that of the precious metals. For this reason, studies are carried out to change the resonance wavelength using doped semiconductor material. But, the doping process is complicated.

Meanwhile, it is of great importance to process a source material to have precise patterns in order to obtain resonance signals at wanted wavelength region using the localized surface plasmon resonance sensor. For this, electron beam (e-beam) lithography is employed for nanostructures and photolithography is employed for larger structures.

However, since these top-down processes are complicated and expensive, they are not suited for applications where a lot of inexpensive sensors are required such as biological or ecological detection. Although bottom-up type self-assembling processes are attempted to overcome this problem, it is difficult to obtain the desired patterns accurately.

REFERENCES OF THE RELATED ART

Patent Documents (Patent document 1) Korean Patent Publication No. 10-2011-0042848

SUMMARY

In an aspect of the present disclosure, a localized surface plasmon resonance (LSPR) sensor wherein a chalcogenide material is used in an LSPR excitation layer and carrier density may be changed variously depending on the composition of the chalcogenide material may be provided.

In another aspect of the present disclosure, a method for manufacturing an LSPR sensor whereby an LSPR excitation layer may be patterned easily to have a desired structure using laser without resorting to the complicated and expensive lithography process may be provided.

A localized surface plasmon resonance sensor according to an exemplary embodiment may include a localized surface plasmon excitation layer including a chalcogenide material. The chalcogenide material may include: a first material including at least one of selenium (Se) and tellurium (Te); and a second material including at least one of germanium (Ge) and antimony (Sb).

A method for manufacturing a localized surface plasmon resonance sensor according to an exemplary embodiment may include: forming a thin film including a chalcogenide material comprising a first material including at least one of selenium (Se) and tellurium (Te) and a second material including at least one of germanium (Ge) and antimony (Sb); and forming a localized surface plasmon excitation layer having a predetermined pattern by irradiating laser on the thin film.

According to the present disclosure, carrier density of the LSPR excitation layer may be changed variously by controlling the composition of the chalcogenide material constituting the LSPR excitation layer and an LSPR sensor that may operate in the infrared region may be provided. The LSPR excitation layer may be formed to have a desired structure via simple direct writing using laser without resorting to the complicated and expensive lithography process.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
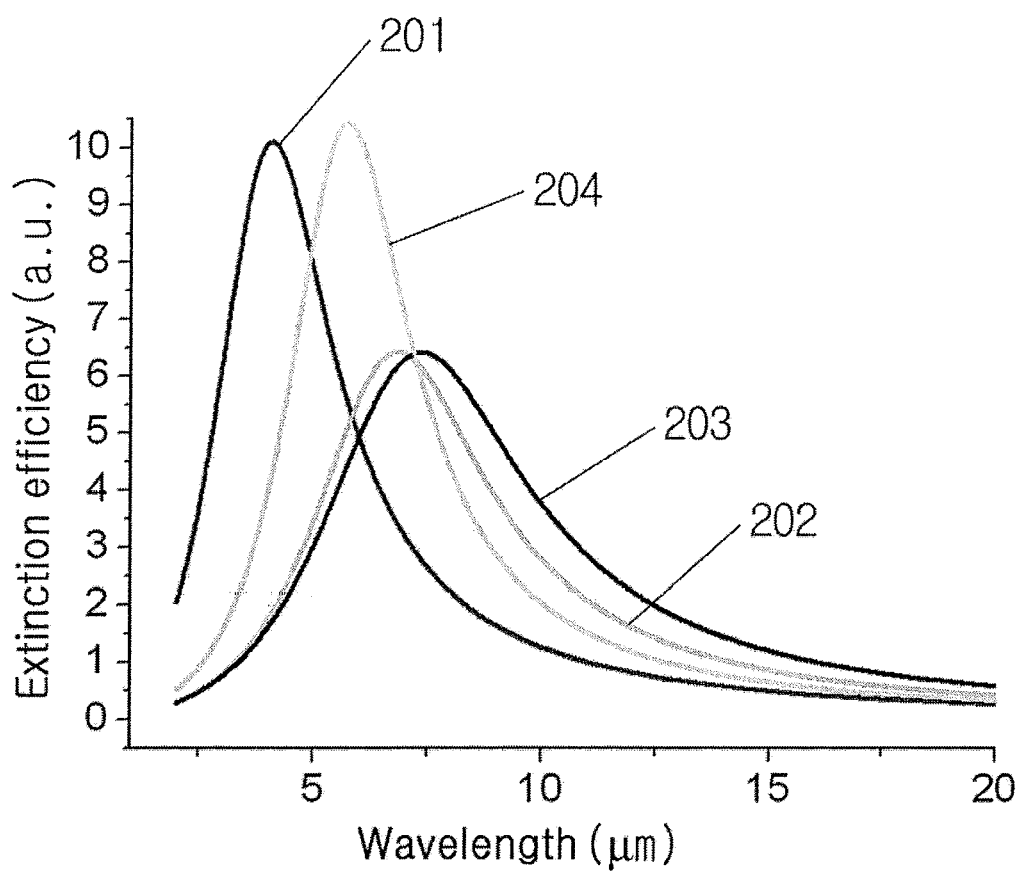
FIG. 1 shows extinction efficiency spectra of a localized surface plasmon resonance sensor according to an exemplary embodiment.

Hereinafter, embodiments of the present disclosure will be described in detail referring to the attached drawings.

A localized surface plasmon resonance (LSPR) sensor according to an exemplary embodiment may comprise a light source, an LSPR excitation layer and a detector. The light source may irradiate light to the LSPR excitation layer. The LSPR excitation layer generates localized surface plasmons as being excited by incident light of a specific resonance wavelength. As a result, at the resonance wavelength, most of light energy is transferred to free electrons in the LSPR excitation layer. The detector may detect a light absorption signal and/or a light scattering signal by detecting light penetrating the LSPR excitation layer or reflected on the LSPR excitation layer.

The LSPR phenomenon is characterized by light absorption associated with the resonance and light scattering associated with energy relaxation. Accordingly, the characteristics of the LSPR resonance may be determined by recording the light absorption signal and/or the light scattering signal as spectrum and analyzing the wavelength of the spectral peaks and the intensity of the peaks. Since the resonance wavelength at which LSPR occurs is very sensitively dependent on the change in medium surrounding the LSPR excitation layer, presence and/or state of the medium surrounding the LSPR excitation layer may be detected using the signal detected by the detector.

In an exemplary embodiment, the light source may irradiate infrared light to the LSPR excitation layer as incident light. The air coming out of the human lungs contain various biomarkers allowing diagnosis of diseases. The wavelength allowing detection of the biomarkers is usually in the mid-infrared region. Some exemplary biomarkers, diseases corresponding to the biomarkers and detection wavelength thereof are described in Table 1. The detection wavelength of carbon dioxide given in Table 1 may be used as a reference wavelength for detection of other biomarkers.

TABLE 1

| Biomarkers | Diseases | Detection wavelength (μm) |
|---|---|---|
| Acetone ($OC(CH_3)_2$) | Lung cancer, diabetes, dietary fat loss, congestive heart failure | 0.266 |
| Acetaldehyde ($CH_3CHO$) | Alcoholism, liver disease, lung cancer | 5.97 |
| Ammonia ($NH_3$) | Kidney disease, asthma | 9-10.7, 10.0, 11.0, 10.3, 1.5 |
| Carbon monoxide (CO) | Oxidative stress, respiratory infection, anemia | 1.6, 4.6, 4.88 |
| Carbon dioxide ($CO_2$) ($^{13}$C-isotope) | Oxidative stress | 4.23 |
| Carbon dioxide ($CO_2$) | | 1.6, 1.59, 4.9, 4.8, 5.2 |
| Carbonyl sulfide (OCS) | Liver disease | 4.86, 4.9 |
| Ethane ($C_2H_6$) | Infantile vitamin E deficiency, lipid peroxidation, oxidative stress | 3.4, 3.0 |
| Ethylene ($C_2H_4$) | Lipid peroxidation, UV-induced skin damage | 10.5 |
| Methane ($CH_4$) | Bowel disorder, colonic fermentation | 3.35 |
| Nitrogen monoxide (NO) | Asthma, bronchiectasis, hypertension, rhinitis, lung disease | 5.2 |

As seen from Table 1, the detection wavelength of many biomarkers is in the infrared region. Accordingly, the light source may be configured to irradiate infrared light. For example, it may be configured to irradiate light in the wavelength region including the detection wavelength of one or more specific biomarker(s). If the LSPR excitation layer of the LSPR sensor comprises a material excited by the infrared light, the LSPR sensor may be used as a biochemical sensor for detecting biomarker(s) and may be utilized variously in the field of medicine, environment, etc.

The LSPR excitation layer of an LSPR sensor according to an exemplary embodiment may comprise a chalcogenide material. The chalcogenide material may comprise a first material comprising selenium (Se) and/or tellurium (Te) and a second material comprising germanium (Ge) and/or antimony (Sb). For example, the LSPR excitation layer may comprise a chalcogenide material wherein germanium (Ge), antimony (Sb) and tellurium (Te) are mixed at specific proportion. And, the chalcogenide material may further comprise one or more additive(s) other than the above-described materials.

It is known that the LSPR resonance wavelength is dependent on the density of carriers (i.e., electrons or holes) in the LSPR excitation layer. Accordingly, the LSPR resonance wavelength may be shifted to the infrared region by adjusting the carrier density of the LSPR excitation layer. In an exemplary embodiment, the carrier density of the LSPR excitation layer comprising the chalcogenide material may be controlled by adjusting the proportion of the elements constituting the chalcogenide material. That is to say, the composition of the chalcogenide material may be determined such that the LSPR resonance wavelength lies in the infrared region.

For example, the inventors of the present disclosure have found out that the carrier density and mobility of the LSPR excitation layer comprising germanium (Ge), antimony (Sb) and tellurium (Te) change as described in Table 2 as the proportion of the elements is varied.

TABLE 2

| Ge:Sb:Te | Carrier density ($\times 10^{20}/cm^3$) | Mobility ($cm^2/Vs$) |
|---|---|---|
| 14:29:57 | 1.81 | 23.90 |
| 0:81:19 | 6.45 | 14.69 |
| 8:60:32 | 9.71 | 6.43 |
| 5:78:17 | 14.00 | 15.11 |
| 13:71:16 | 18.90 | 10.46 |
| 5:71:23 | 24.10 | 10.49 |

And, Table 3 shows the optical properties of the LSPR excitation layer comprising germanium (Ge), antimony (Sb) and tellurium (Te) depending on the proportion of the elements.

TABLE 3

| Ge:Sb:Te | $\epsilon_\infty$ | $\tau$ ($10^{-15}$ s) | $\sigma_{dc}$ ($\Omega$ cm)$^{-1}$ | $\omega_p$ ($10^{14}$ rad/s) |
|---|---|---|---|---|
| 50:0:50 | 57.1 | 2.78 | 3121 | 4.71 |
| 22:22:56 | 60.6 | 5.29 | 2230 | 2.80 |
| 14:29:57 | 51.7 | 5.23 | 1637 | 2.61 |
| 8:34:58 | 52.6 | 5.27 | 2754 | 3.35 |

In Table 3, $\epsilon_\infty$, $\tau$, $\sigma_{dc}$ and $\omega_p$ are optical parameters of the LSPR excitation layer at the given proportion of germanium (Ge), antimony (Sb) and tellurium (Te). $\epsilon_\infty$ is the dielectric constant when the frequency of a signal is infinite, $\tau$ is the relaxation time, $\sigma_{dc}$ is the conductivity for a DC electrical signal and $\omega_p$ is the plasma frequency.

The LSPR resonance wavelength of the LSPR excitation layer is determined by the above-described optical parameters and the extinction efficiency of the LSPR excitation layer may be calculated from the optical parameters based on the Drude model. A detailed description about the computation will be omitted since it can be easily understood by those skilled in the art.

FIG. 1 shows extinction efficiency calculated for the LSPR excitation layers having the composition described in Table 3.

Referring to FIG. 1, the four curves 201, 202, 203 and 204 respectively correspond to the LSPR excitation layers having the composition described in Table 3. That is to say, the curve 201 represents the extinction efficiency of the LSPR excitation layer whose Ge:Sb:Te ratio is 50:0:50, the curve 202 represents the extinction efficiency of the LSPR excitation layer whose Ge:Sb:Te ratio is 22:22:56, the curve 203 represents the extinction efficiency of the LSPR excitation layer whose Ge:Sb:Te ratio is 14:29:57 and the curve 204 represents the extinction efficiency of the LSPR excitation layer whose Ge:Sb:Te ratio is 8:34:58.

When LSPR occurs, light absorption and/or scattering by the LSPR excitation layer increases, and, this leads to increased extinction efficiency. Accordingly the wavelengths at which the peaks are observed in the curves 201, 202, 203 and 204 of FIG. 1 correspond to LSPR resonance wavelengths. That is to say, the LSPR resonance wavelength for the curve 201 is about 4.05 μm, the LSPR resonance wavelength for the curve 202 is about 5.71 μm, the LSPR resonance wavelength for the curve 203 is about 6.75 μm and the LSPR resonance wavelength for the curve 204 is about 7.32 μm. Since the LSPR resonance wavelength lies in the near-infrared, mid-infrared and far-infrared regions, an LSPR-based infrared sensor may be manufactured using the LSPR excitation layer having the composition described in Table 3.

The carrier density of the LSPR excitation layer of the LSPR sensor may be controlled by adjusting the composition of the LSPR excitation layer comprising the chalcogenide material and the LSPR sensor may operate in the infrared region. Whereas the existing LSPR sensor uses doped semiconductor material to extend the wavelength region, the LSPR sensor according to the present disclosure required no doping and the LSPR resonance wavelength may be easily controlled by variously adjusting carrier density through control of the proportion of the elements in the chalcogenide material.

Hereinafter, a method for manufacturing an LSPR sensor comprising an LSPR excitation layer comprising a chalcogenide material according to an exemplary embodiment will be described.

In an exemplary embodiment, an LSPR excitation layer comprises a chalcogenide material whose phase changes by heat treatment. The chalcogenide material is amorphous phase in the as-deposited state and has nonmetallic, i.e. dielectric-like, property in the infrared region. But, after heat treatment, the chalcogenide material is converted to crystalline and exhibits metallic property. Accordingly, an LSPR excitation layer comprising a crystalline chalcogenide material may be formed by direct laser writing.

Figure 2:
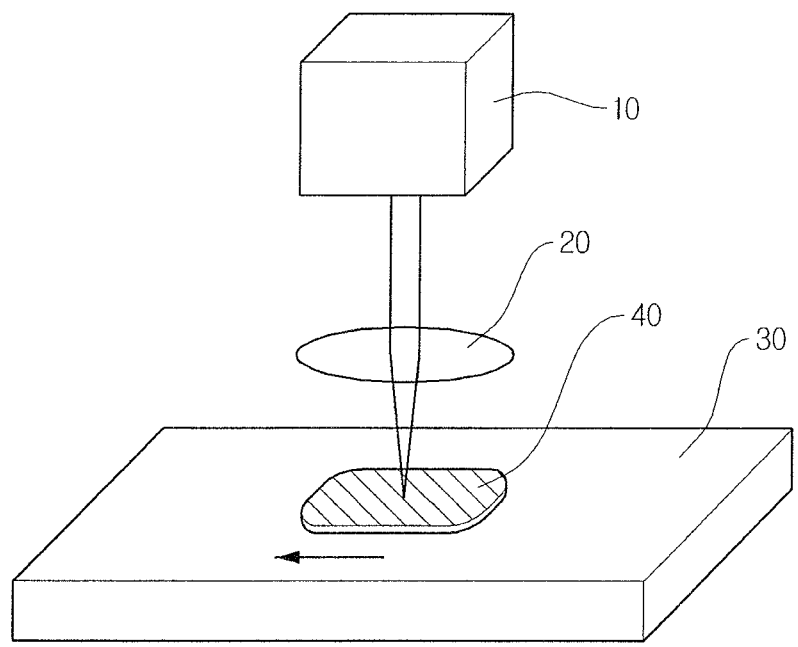
FIG. 2 schematically illustrates a method for manufacturing a localized surface plasmon resonance sensor according to an exemplary embodiment.

FIG. 2 schematically illustrates a method for manufacturing a localized surface plasmon resonance sensor according to an exemplary embodiment.

Referring to FIG. 2, a thin film 40 comprising a chalcogenide material may be formed on a substrate 30. The substrate 30 serves as a space for forming an LSPR excitation layer and may comprise a dielectric material although not being limited thereto. The substrate 30 may be either included as a part of the finally manufactured LSPR sensor or may be removed or separated from the LSPR sensor. The thin film 40 may be formed by sputtering or other adequate method and is amorphous phase in the as-formed state.

Those skilled in the art will easily understand that the substrate 30, the thin film 40, etc. illustrated in FIG. 2 are given only as an example to describe the process of manufacturing the LSPR excitation layer and their actual locations, sizes or shapes may be different.

After the thin film 40 is formed, the thin film 40 may be crystallized by irradiating laser. For example, a laser beam may be irradiated using a light source 10 and the laser beam may be converged on the thin film 40 using a prism 20. Since the thin film 40 comprises the chalcogenide material whose phase is changeable, irradiation of laser of an adequate intensity to the thin film 40 may result in crystallization of the laser-irradiated region owing to heat. The LSPR excitation layer may be formed by crystallizing the thin film 40 to have a predetermined pattern in this manner. The crystallized pattern may be a 3-dimensional structure pattern capable of generating LSPR. For example, the 3-dimensional structure may be a nanostructure such as a nanodisc, a nanorod, etc., but is not limited thereto.

In an exemplary embodiment, to crystallize the thin film 40 to have the 3-dimensional structure, the laser may be irradiated while changing the irradiation location of laser on the thin film 40. For example, the irradiation location of laser on the thin film 40 may be changed by moving the thin film 40 with the light source 10 fixed or by moving the light source 10 with the thin film 40 fixed. Also, the size and shape of the crystallized region of the thin film 40 may be controlled by the intensity of laser, the moving speed of laser, the pulse length of laser, or the like.

Instead of crystallizing the thin film by directly irradiating laser according to the pattern shape, the pattern may be formed by irradiating a plurality of coherent laser beams in another exemplary embodiment. The plurality of coherent laser beams may be irradiated to the thin film 40 such that an interference pattern is formed by the laser beams. In this case, an array structure may be formed by adjusting the crystallizing region according to the intensity of laser using the difference in constructive interference and destructive interference of the interference pattern. For example, the size and shape of the crystallized region of the thin film 40 may be determined according to the interference pattern by adjusting, for example, the intensity of the coherent laser beams such that the thin film 40 is crystallized at the region corresponding to the constructive interference and the thin film 40 is not crystallized at the region corresponding to the destructive interference.

A laser-unirradiated region of the thin film 40, which remains amorphous state, may be removed. As a result, only the crystallized region may remain to form the LSPR excitation layer. For example, after the thin film 40 is crystallized according to the predetermined pattern, selective wet etching may be carried out using a tetramethylammonium hydroxide (TMAH) solution. By adjusting the concentration of the TMAH solution, only the amorphous region may be selectively removed from the thin film 40 except for the crystallized region. For example, selective wet etching may be carried out using a TMAH solution with a concentration of about 25%.

Thus formed LSPR excitation layer may be assembled with a light source and a detector to manufacture an LSPR sensor. According to the method for manufacturing an LSPR sensor described above, a desired structure may be prepared easily by direct laser writing without resorting to the costly lithography process.

While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A method for manufacturing a localized surface plasmon resonance sensor, comprising:
    forming a thin film comprising a chalcogenide material comprising a first material comprising at least one of selenium (Se) and tellurium (Te) and a second material comprising at least one of germanium (Ge) and antimony (Sb); and
    forming a localized surface plasmon excitation layer having a predetermined pattern by irradiating laser on the thin film, wherein the thin film is amorphous state and said forming the localized surface plasmon excitation layer comprises crystallizing the chalcogenide material with laser.

2. The method for manufacturing a localized surface plasmon resonance sensor according to claim 1, wherein said crystallizing the chalcogenide material with laser comprises changing the irradiation location of laser according to the predetermined pattern.

3. The method for manufacturing a localized surface plasmon resonance sensor according to claim 2, wherein said crystallizing the chalcogenide material with laser comprises adjusting one or more of the intensity of laser, the moving speed of laser and the pulse length of laser.

4. The method for manufacturing a localized surface plasmon resonance sensor according to claim 1, wherein said crystallizing the chalcogenide material with laser comprises irradiating a plurality of coherent laser beams to the thin film.

5. The method for manufacturing a localized surface plasmon resonance sensor according to claim 4, wherein the predetermined pattern corresponds to an interference pattern formed by the plurality of coherent laser beams.

6. The method for manufacturing a localized surface plasmon resonance sensor according to claim 1, wherein said forming the localized surface plasmon excitation layer further comprises removing a laser-unirradiated region from the thin film.

7. The method for manufacturing a localized surface plasmon resonance sensor according to claim 1, wherein said forming the thin film comprises forming the thin film by sputtering.

8. The method for manufacturing a localized surface plasmon resonance sensor according to claim 1, wherein said forming the thin film comprises controlling carrier density of the thin film by adjusting the composition of the chalcogenide material.

* * * * *